(12) United States Patent
Varasani

(10) Patent No.: US 12,226,560 B2
(45) Date of Patent: Feb. 18, 2025

(54) DIALYSIS FILTER SYSTEM

(71) Applicant: Bellco S.R.L., Mirandola (IT)

(72) Inventor: Michele Varasani, SantAgata Bolognese (IT)

(73) Assignee: Bellco S.R.L., Mirandola (IT)

( * ) Notice: Subject to any disclaimer, the term of this patent is extended or adjusted under 35 U.S.C. 154(b) by 0 days.

(21) Appl. No.: 17/812,466

(22) Filed: Jul. 14, 2022

(65) Prior Publication Data

US 2023/0014595 A1 Jan. 19, 2023

Related U.S. Application Data

(60) Provisional application No. 63/221,765, filed on Jul. 14, 2021.

(51) Int. Cl.
*A61M 1/16* (2006.01)
*A61M 1/34* (2006.01)

(52) U.S. Cl.
CPC ............ *A61M 1/3401* (2022.05); *A61M 1/16* (2013.01); *A61M 1/3413* (2013.01)

(58) Field of Classification Search
CPC ........ A61M 1/34; A61M 1/16; A61M 1/3472; A61M 1/3413; A61M 1/3417; A61M 1/14; A61M 1/3468; A61M 1/3401; A61M 1/1621; A61M 1/1696; A61M 1/3465; A61M 1/3431; A61M 1/3482
See application file for complete search history.

(56) References Cited

U.S. PATENT DOCUMENTS

| 2009/0112146 | A1* | 4/2009 | Wratten | A61M 1/3679 604/5.04 |
| 2015/0283315 | A1* | 10/2015 | Cho | A61M 1/3417 210/314 |
| 2015/0367055 | A1* | 12/2015 | Pudil | B01J 20/0211 423/306 |
| 2021/0283553 | A1* | 9/2021 | Beck | B01D 63/02 |

FOREIGN PATENT DOCUMENTS

| EP | 0780133 A1 | 6/1997 |
| EP | 2762178 A1 | 8/2014 |

OTHER PUBLICATIONS

Pizzarelli et al., "Double-Chamber On-Line Hemodiafiltration: A Novel Technique with Intra-Treatment Monitoring of Dialysate Ultrafilter Integrity", Blood Purif, vol. 18, No. 3, 2000, p. 237-241, (Applicant points out, in accordance with MPEP 609.04(a), that the year of publication, 2000, is sufficiently earlier than the effective U.S. filing date, so that the particular month of publication is not an issue.).

* cited by examiner

*Primary Examiner* — Pranav N Patel

(57) ABSTRACT

In some examples, a filtration assembly for hemodiafiltration therapy includes a filtration body connector configured to removably mechanically connect the filtration assembly and a dialyzer. In examples, the filtration assembly is configured to remain substantially stationary relative to the dialyzer when the filtration assembly mechanically mates with the dialyzer. The filtration body connector is configured to removably mechanically connect the filtration assembly with a plurality of different types of dialyzers, which may be selected based on a prescription for a particular patient.

19 Claims, 4 Drawing Sheets

DIALYSIS FILTER SYSTEM

TECHNICAL FIELD

This application claims the benefit of U.S. Provisional Application Ser. No. 63/221,765, filed Jul. 14, 2021, which is entitled "DIALYSIS FILTER SYSTEM" and is incorporated by reference herein in its entirety.

TECHNICAL FIELD

This disclosure is related to dialysis.

BACKGROUND

Dialysis filters may be used to remove waste products from blood of a patient when the kidneys of the patient are no longer able to adequately do so. During dialysis, a dialysis machine may generate or regenerate dialysate using specified concentrations of solute buffers, osmotic agents, cations, and/or other concentrates for biocompatibility with the patient. A dialysis machine may provide the dialysate to the dialysis filter to cause the dialysate to remove the waste products from the blood of the patient. The dialysis filter may remove the waste products as an aqueous solution during the dialysis treatment.

SUMMARY

This disclosure describes a dialysis filter assembly configured to remove waste products from a blood flow using dialysate during hemodiafiltration reinfusion. The dialysis filter assembly includes a filtration assembly configured to receive and condition the blood flow before providing the blood flow to a dialyzer configured to cause an exchange of waste products with the dialysate. In examples, the filtration assembly is configured to remove a first portion of waste products and the dialyzer is configured to remove a second portion of waste products. The filtration assembly includes a filtration body connector configured to removably mechanically mate with the dialyzer. The dialyzer may be any type of dialyzer, such as a specific dialyzer required for a prescribed hemodialysis treatment of the patient.

The filtration assembly is physically separate from the dialyzer and the filtration body connector is configured to mechanically mate the filtration assembly with a plurality of different types of dialyzers. Thus, the dialysis filter assembly may be assembled in-situ by the clinician based on the prescribed hemodialysis treatment. For example, the clinician may select a dialyzer from a plurality of different available dialyzers and connect the filtration assembly to the selected dialyzer. The filtration body connector of the filtration assembly is configured to connect to each of the plurality of different available dialyzers.

In some examples, a medical system comprises: a filtration membrane including a first side and a second side; and a filtration body defining an interior volume between a proximal end and a distal end, wherein the filtration membrane is positioned within the interior volume, the filtration body comprising: a filtration proximal access at the proximal end configured to receive a blood flow, wherein the filtration proximal access is in fluid communication with the first side of the filtration membrane; a filtrate access in fluid communication with the second side of the filtration membrane; a filtration distal access at the distal end, wherein the filtration distal access is in fluid communication with the first side of the filtration membrane and the filtration proximal access, wherein the filtration distal access is configured to provide at least a portion of the blood flow to a dialyzer; and a filtration body connector secured to the distal end, wherein the filtration body connector is configured to removably mechanically mate with the dialyzer to enable the filtration distal access to provide the portion of the blood flow to the dialyzer.

In some examples, a medical system comprises: a filtration membrane including a first side and a second side; and a filtration body defining an interior volume between a proximal end and a distal end, wherein the filtration membrane is positioned within the interior volume, the filtration body comprising: a proximal cap at the proximal end defining a filtration proximal access configured to receive a blood flow, wherein the filtration proximal access is in fluid communication with the first side of the filtration membrane; a filtrate access in fluid communication with the second side of the filtration membrane; a distal cap at the distal end defining a filtration distal access, wherein the filtration distal access is in fluid communication with the first side of the filtration membrane and the filtration proximal access, wherein the filtration distal access is configured to provide at least a portion of the blood flow to a dialyzer; and a filtration body connector secured to the distal cap, wherein the filtration body connector is configured to removably mechanically mate with the dialyzer to enable the filtration distal access to provide the portion of the blood flow to the dialyzer.

In some examples, a method comprises: mechanically mating a filtration body connector secured to a distal end of a filtration body with a dialyzer, wherein the mechanical mating is a removable mechanical mating, wherein the filtration body defines an filtration proximal access at a proximal end of the filtration body in fluid communication with an first side of a filtration membrane, a filtrate access in fluid communication with a second side of the filtration membrane, and a filtration distal access in fluid communication with the filtration proximal access and the first side of the filtration membrane; and establishing fluid communication between the filtration distal access and the dialyzer when the filtration body connector mechanically mates with the dialyzer.

The details of one or more examples are set forth in the accompanying drawings and the description below. Other features, objects, and advantages will be apparent from the description and drawings, and from the claims.

DETAILED DESCRIPTION

Figure 1:
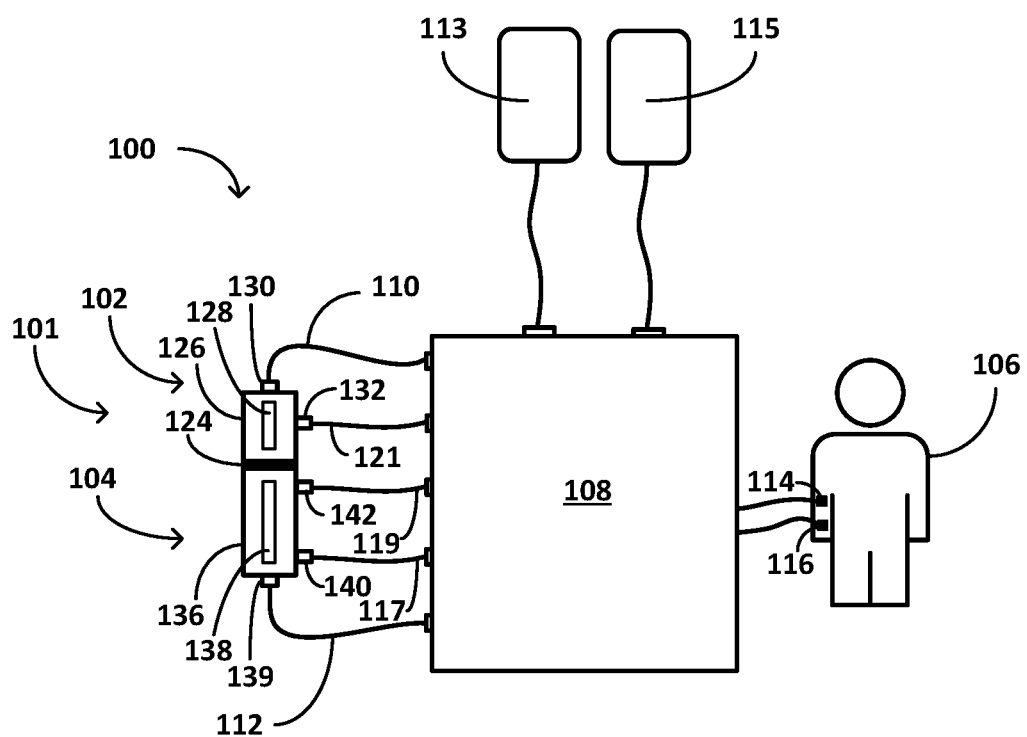
FIG. 1 is a conceptual diagram illustrating an example medical system including a dialysis filter assembly configured to remove waste from a blood flow.

This disclosure describes a medical system including a filtration assembly configured for use during a hemodiafiltration (HDF) reinfusion treatment of a patient. The HDF reinfusion treatment may utilize the filtration assembly in conjunction with a dialyzer supporting a hemodialysis membrane. The filtration assembly includes a filtration membrane supported by a filtration body. The filtration body is configured to receive a blood flow from an arterial line of a dialysis machine configured to receive the blood flow from the patient. The filtration body is configured to cause the filtration membrane to condition the blood flow before providing the conditioned blood flow to the dialyzer. The dialyzer may be configured to receive the conditioned blood flow and a dialysate from the dialysis machine and cause the dialysate to remove waste products from the conditioned blood using the hemodialysis membrane. The dialyzer may be configured to return the processed (e.g., cleansed) blood to the dialysis machine for return to the patient.

The filtration body and the dialyzer thus function to remove waste products from the blood of the patient by operating in a sequential manner, wherein the filtration body receives a blood flow from an arterial line of a dialysis machine and issues some portion of the received blood flow to the dialyzer. Acting in conjunction, the filtration body (e.g., the filtration membrane) and the dialyzer remove waste products from the blood flow received from the dialysis machine and return a cleansed blood flow to the dialysis machine. The cleansed blood can include, for example, blood that has fewer waste products than the arterial blood received by the filtration body.

In some examples, the filtration membrane is configured to condition the blood flow received by the filtration body by at least convecting an aqueous solution containing waste products from the blood flow prior to the filtration body providing at least a portion of the blood flow to the dialyzer. The filtration membrane may be configured to remove, for example, lower and middle molecular weight waste products via the convection. The filtration membrane may substantially split the received blood flow by at least convecting a first portion of the blood flow containing the aqueous solution from an influent side to an effluent side of the filtration membrane as a second portion of the blood flow (e.g., the unconvected portion) remains on the influent side. The filtration body may be configured to discharge the first portion of the blood flow as a filtrate through a filtrate access defined by the filtration body, and provide the second portion of the blood flow to the dialyzer through a filtration distal access defined by the filtration body. The dialyzer may be configured to cause waste products in the second portion of the blood flow (e.g., large molecular weight waste products) to diffuse across the hemodialysis membrane into the dialysate. In examples, the filtration body is configured to discharge the filtrate (e.g., the first portion of the blood flow) to a dialysis machine. The dialysis machine may substantially purify the filtrate using resins, additional filters, and/or other purification elements to generate a reinfusion fluid suitable for infusion into the blood of the patient, to assist in maintain a hydration state of the patient during the hemodialysis treatment.

In some examples, the filtration membrane is configured to condition the blood flow received by the filtration body by merging a reinfusion fluid with the blood flow prior to the filtration body providing at least a portion of the blood flow to the dialyzer. The filtration body may support the filtration membrane such that the filtration membrane receives the infusion fluid from the filtrate access and passes the reinfusion fluid from an influent side to an effluent side to filter the reinfusion fluid. The filtration membrane may be configured such that the blood flow received by the filtration body substantially remains on the effluent side as the filtration membrane passes the reinfusion fluid. The filtration body may merge the received blood flow and the reinfusion fluid and provide the merged blood flow to the dialyzer via the filtration distal access of the filtration body. The dialyzer may be configured to remove waste products from the merged blood flow by causing the waste products to diffuse and/or convect across the hemodialysis membrane into the dialysate.

The filtration body and the dialyzer are thus configured to fluidly communicate in order to filter the blood flow received by the filtration body and generate a substantially cleansed blood flow issuing from the dialyzer. In examples, the dialyzer includes a dialyzer body mechanically supporting the hemodialysis membrane, and the filtration body includes a filtration body connector configured to removably mechanically connect the filtration body with the dialyzer body to provide the fluid communication. The filtration body may be configured to mechanically connect with the dialyzer body such that the filtration distal access of the filtration body provides a conditioned blood flow (e.g., the second portion of the blood flow, or the merged blood flow) to the dialyzer. In examples, the filtration body and the dialyzer body are configured to mechanically connect to cause the filtration body and the dialyzer body to substantially act as a unified body, such that, for example, the filtration body and the dialyzer body substantially behave as a unified object when handled by a clinician. Configuring the filtration body and the dialyzer body to behave as a unified object may ease the set-up and administration of a dialysis treatment by, for example, reducing a number of separate tubing connections, securing both the filtration body and the dialyzer body using a single mechanism (e.g., a single bracket of a dialysis machine), reducing a number of procedural set-up steps required by a clinician, or other reasons.

The filtration assembly includes a filtration body connector configured to mechanically mate with a plurality of different types of dialyzers. The filtration assembly is configured to allow a clinician to mechanically mate the filtration assembly to a specific dialyzer required for a prescribed hemodialysis treatment of a patient. That is, the clinician may select a dialyzer from a plurality of different types of dialyzers and mechanically and fluidically connect the selected dialyzer to the filtration assembly via the filtration body connector. The filtration assembly and dialyzer may thus be assembled in-situ by a clinician based on the prescribed hemodialysis treatment. This may provide advantage compared to dual-filter hemodialysis assemblies which have a permanent connection between a first chamber holding a filtration membrane and a second chamber holding a hemodialysis membrane. Such permanently connected dual-filter hemodialysis assemblies require connection at the point of manufacturing assembly, such that the hemodialysis treatments delivered at a treatment location become dependent on supply logistics associated with the previously manufactured dual-filter assemblies.

The medical system disclosed herein includes a filtration assembly including a filtration body. The filtration body is configured to mechanically mate with a dialyzer such that the filtration body may provide a blood flow to a dialyzer. The filtration body defines a filtration proximal access at a proximal end of the filtration body ("filtration proximal end") and a filtration distal access at a distal end of the filtration body ("filtration distal end"). The filtration proximal access and the filtration distal access are in fluid communication with an interior volume defined by the filtration body. In examples, the filtration proximal access is configured to receive the blood flow into the interior volume and the filtration distal access is configured to discharge some portion of the blood flow from the interior volume to the dialyzer. The filtration body may be configured such that removably mechanically mating the filtration body with the dialyzer establishes fluid communication between the filtration distal access and the dialyzer. In examples, the filtration body is configured to removably mechanically mate with the dialyzer substantially through the application of hand force to the filtration body, such that the mechanical mating may be achieved by a clinician without any special tools.

The filtration body further defines a filtrate access in fluid communication with the interior volume. In some examples, the filtrate access is configured to convey a first portion of the blood flow from the interior volume as the filtration distal end provides a second portion of the blood flow to the dialyzer. In some examples, the filtrate access is configured to provide a reinfusion fluid to the interior volume, such that the filtration distal access provide a merged flow comprising the blood flow and reinfusion fluid to the dialyzer.

The filtration assembly is configured to mechanically support a filtration membrane within the interior volume. The filtration membrane defines a first side and a second side and is configured to allow a fluid to pass between the first side and the second side. In examples, the filtration membrane supported such that filtration membrane is substantially interposed between the filtrate access and at least one of the filtration proximal access or the filtration distal access. For example, the filtration body may mechanically support the filtration membrane such that a fluid crosses the filtration membrane when the fluid flows between filtrate access and at least one of the filtration proximal access or the filtration distal access.

In examples, the filtration body is configured to receive the blood flow via the filtration proximal access and provide a first portion of the blood flow to the filtrate access and a second portion of the blood flow to the filtration distal access. The filtration membrane may be positioned (e.g., mechanically supported) within the interior volume such that the first portion passes from the first side to the second side of the filtration membrane when the filtration body provides the first portion to the filtrate access. In examples, the filtration membrane is a convective membrane configured to convey an aqueous solution of one or more uremic toxins from the blood flow when the first portion passes from the first side to the second side. In examples, the filtration body is configured to maintain a positive pressure across the filtration membrane from the first side to the second side.

In examples, the filtration body is configured to receive the blood flow via the filtration proximal access and merge the blood flow and a reinfusion fluid received via the filtrate access. The filtration membrane may be positioned (e.g., mechanically supported) within the interior volume such that the reinfusion fluid passes from the second side to the first side of the filtration membrane when the filtration body merges the blood flow and the reinfusion fluid. In examples, the filtration membrane is configured to filter one or more impurities from the reinfusion fluid when the reinfusion fluid passes from the second side to the first side. In examples, the filtration body is configured to maintain a positive pressure across the filtration membrane from the second side to the first side.

The filtration assembly may be configured to mechanically mate with a plurality of different types of dialyzers. In examples, the filtration assembly (e.g., the filtration body) defines a filtration body connector configured to mechanically mate with a connector defined by a dialyzer body ("dialyzer body connector"). For example, the filtration body connector may include a bearing structure configured to transmit a force from the filtration body to the dialyzer or from the dialyzer to the filtration body when the filtration body connector mechanically mates with the dialyzer, such that the filtration assembly and the dialyzer may be handled (e.g., by a clinician) as a substantially unified object. The filtration body connector may be configured to mechanically mate with the dialyzer using hand force, such that the filtration assembly may be mechanically mated in-situ by the clinician to a specific type of dialyzer called for by the prescribed hemodialysis for a patient. For example, the filtration body connector may include a set of screw threads configured to threadably engage a dialysis body connector of a dialyzer to achieve the mechanical mating. As another example, the filtration body connector may include a structure configured to form a snap-fit with dialysis body connector of a dialyzer to achieve the mechanical mating.

In examples, the filtration proximal access, the filtrate access, and/or the distal filtration access may include one or more visible indications that helps a clinician or other user properly connect the filtration assembly to a hemodialysis machine and/or a dialyzer. For example, the filtration proximal access may have a color and/or include a marking (e.g., a graphical marking, an alphanumeric marking, and/or the like) corresponding to a color and/or marking of an arterial line of a hemodialysis machine. The filtrate access may have a color and/or include a marking corresponding to a color and/or marking of a line of the hemodialysis machine configured to receive the first portion of the blood flow from the filtrate access, or provide the reinfusion fluid to the filtrate access. The distal filtration access and/or filtration body connector may have a color and/or include a marking corresponding to a color and/or marking of a dialyzer body connector configured to mechanically mate with the filtration body connector.

In addition to, or instead of, the visible indications, the filtration proximal access, the filtrate access, and/or the distal filtration access may be configured to mate with a specific mechanical fitting of the hemodialysis machine or the dialyzer and to not mate with other mechanical fittings of the hemodialysis machine or the dialyzer. For example, the filtration proximal access, the filtrate access, and/or the distal filtration access may have corresponding dimensions and/or shapes that indicate to a user which specific mechanical connection of the hemodialysis machine or dialyzer is configured to connect with the filtration proximal access, the filtrate access, or the distal filtration access of the filtration assembly.

Hence, the medical system disclosed includes a filtration assembly configured to mechanically mate with a dialyzer for the delivery of a prescribed hemodialysis treatment to a patient. The filtration assembly is configured to act in conjunction with the dialyzer to remove waste products from a blood flow received by the filtration assembly. The dialyzer may be configured to return the substantially cleansed blood to the dialysis machine for return to the patient. The filtration assembly may be mechanically mated to a variety of different dialyzers to deliver the prescribed hemodialysis treatment. In examples, the filtration assembly may be mechanically mated with a dialyzer using hand force and without any special tools. The filtration assembly and dialyzer may thus be assembled in-situ by a clinician based on a specific type of dialyzer called for by the prescribed hemodialysis treatment.

FIG. 1 illustrates a schematic block diagram of an example medical system 100 including a dialysis filter assembly 101 including filtration assembly 102 and a dialyzer 104. Dialysis filter assembly 101 is configured to remove waste products from the blood of a patient 106. A medical machine 108 is configured to deliver the blood flow from patient 106 to dialysis filter assembly 101 via an arterial line 110 of medical machine 108. Medical machine 108 may be is configured to provide renal replacement therapy (e.g., HDF) to patient 106. In examples, filtration assembly 102 and dialyzer 104 are configured to operate in a sequential manner, such that filter assembly 101 receives the blood flow from arterial line 110 and issues at least some portion of the received blood flow to dialyzer 104. Dialysis filter assembly 101 is configured to remove waste products from the blood flow received and return a cleansed blood flow to medical machine 108 via venous line 112. Medical machine 108 may be configured to receive a blood from patient 106 using a first medical device 114 and provide the cleansed blood flow from venous line 112 to patient 106 using a second medical device 116. First medical device 114 and/or second medical device 116 may be, for example, the same (e.g., defined by respective lumens) or different catheters or another medical device configured to receive and/or provide a flow of blood to and/or from patient 106.

In examples, dialysis filter assembly 101 is configured to receive dialysate from medical machine 108 to cause waste products to pass to the dialysate as blood flows through dialysis filter assembly 101 from arterial line 110 to venous line 112. Medical machine 108 may be configured to generate the dialysate using one or more dialysate bags, such as bag 113 and/or bag 115. Medical machine 108 may be configured to provide the dialysate to dialysis filter assembly 101 using one or more fluid lines such as fluid line 117 and/or fluid line 119. In examples, medical machine 108 is configured to provide dialysate (e.g., a clean dialysate) to dialysis filter assembly 101 using one of fluid line 117 or fluid line 119 and receive the dialysate (e.g., a spent dialysate) from dialysis filter assembly 101 from the other of fluid line 117 or fluid line 119. Dialysis filter assembly 101 may be configured to cause waste products to pass from the blood flow received via arterial line 110 to the flow of dialysate received from medical machine 108 before discharging a cleansed blood flow to venous line 112. In some examples, dialysis filter assembly 101 is configured to cause blood flow to flow from arterial line 110 to venous line 112 in a first direction and cause the dialysate to flow within dialysis filter assembly 101 in a second direction substantially opposite the first direction, such that dialysis filter assembly 101 enables a cross-current flow exchange between the blood flow and the dialysate.

Dialysis filter assembly 101 may be a dual chamber filter assembly configured to remove waste products from a blood flow through diffusion, convection, or a combination of diffusion and convection. In examples, dialysis filter assembly 101 is configured to diffusively remove waste products by substantially maintaining a positive pressure across a membrane to cause waste products to diffuse from the blood flow across the membrane. In examples, dialysis filter assembly 101 is configured to convectively remove waste products by substantially maintaining a positive pressure across a membrane (e.g., the same or a different membrane as that used for diffusive removal) to cause an aqueous solution of waste products from the blood flow to flow across the membrane. Dialysis filter assembly 101 may be configured to remove waste products diffusively, convectively, of diffusively and convectively using either of filtration assembly 102 or dialyzer 104.

Dialysis filter assembly 101 may be configured to enable medical machine 108 to generate a reinfusion fluid using the blood flow received via arterial line 110. Medical machine 108 may be configured to generate the reinfusion fluid to, for example, facilitate hydration of patient 106 during a hemodialysis treatment. In examples, dialysis filter assembly 101 is configured to provide a portion of the blood flow received to medical machine 108 to enable medical machine 108 to generate the reinfusion fluid. In some examples, dialysis filter assembly 101 is configured to provide a portion of the blood flow received to medical machine 108 via a fluid line 121 in fluid communication with filtration assembly 102. In some examples, dialysis filter 101 is configured to provide a portion of the blood flow received to medical machine 108 via fluid line 119 and/or fluid line 117. Medical machine 108 may be configured to at least partially purify the portion of the blood flow received from dialysis filter assembly 101 using resins, additional filters, and/or other purification elements to generate a reinfusion fluid suitable for infusion into the blood of patient 106. Dialysis filter assembly 101 may be configured to receive the reinfusion fluid from medical machine 108 and merge the reinfusion fluid with a blood flow within dialysis filter assembly 101, such that substantially cleansed blood delivered via venous line 112 includes the reinfusion fluid.

Dialysis filter assembly 101 is configured such that filtration assembly 102 and dialyzer 104 substantially act as a unified body, such that, for example, filtration assembly 102 and dialyzer 104 substantially behave as a unified object when handled by a clinician. In examples, although filtration assembly 102 and dialyzer 104 are physically separate components, filtration assembly 102 and dialyzer 104 are substantially secured (e.g., mechanically connected) to one another by a connecting joint 124 configured to cause filtration assembly 102 and dialyzer 104 to substantially act as a unified body. Connecting joint 124 may be configured such that at least a portion of a force exerted on one of filtration assembly 102 or dialyzer 104 is transmitted to the other of filtration assembly 102 or dialyzer 104 through connecting joint 124. In examples, connecting joint 124 is configured such that filtration assembly 102 remains substantially stationary, e.g., via a rigid connection, with respect to dialyzer 104, and vice-versa, when filtration assembly 102 and dialyzer 104 are connected. In some examples, connecting joint 124 is configured to mechanically mate filtration assembly 102 and dialyzer 104. The use of connecting joint 124 to cause filtration assembly 102 and dialyzer 104 to behave as a unified object may ease the set-up and administration of a dialysis treatment by, for example, reducing a number of separate tubing connections, securing both filtration body 126 and dialyzer body 136 using a single mechanism (e.g., a single bracket of a dialysis machine), reducing a number of procedural set-up steps required by a clinician, or other reasons.

Filtration assembly 102 includes a filtration body 126 configured to mechanically support a filtration membrane 128. Filtration body 126 defines a filtration proximal access 130 configured to receive a blood flow (e.g., from arterial line 110). In examples, filtration membrane 128 is configured to condition the blood flow received via filtration proximal access 130 prior to providing at least a portion of the blood flow to dialyzer 104. In examples, filtration membrane 128 is configured to convect and/or diffuse a first portion of the blood flow received via filtration proximal access 130 from a first side of filtration membrane 128 to a second side of filtration membrane 128. The first portion may include an aqueous solution containing waste products from the blood flow. Filtration body 126 may be configured to discharge a filtrate containing the first portion of the blood flow to medical machine 108 and provide a second portion of the blood flow to dialyzer 104. Medical machine 108 may be configured to receive the filtrate from filtrate access 132 via fluid line 121. In examples, medical machine 108 is configured to substantially purify the filtrate received to generate a reinfusion fluid.

In some examples, filtration body 126 is configured to condition the blood flow received via filtration proximal access 130 by merging a reinfusion fluid with the blood flow prior to filtration body 126 providing the blood flow to dialyzer 104. Filtration body 126 may support filtration membrane 128 such that the reinfusion fluid received through filtrate access 132 passes through filtration membrane 128 prior to merging the reinfusion fluid with the blood flow. In examples, filtration body 126 is configured to receive the reinfusion from medical machine 108. Medical machine 108 may be configured to provide the reinfusion fluid to filtrate access 132 via fluid line 121.

Filtration body 126 is configured to provide at least a portion of the blood flow received via filtration proximal access 130 to dialyzer 104. Dialyzer 104 includes a dialyzer body 136 configured to mechanically support a hemodialysis membrane 138. In examples, hemodialysis membrane 138 is configured to convect and/or diffuse a uremic toxin from a blood stream contacting hemodialysis membrane 138. Hemodialysis membrane 138 may be configured to convect and/or diffuse waste products from the blood flow received from filtration assembly 102. In examples, dialyzer body 136 supports hemodialysis membrane 138 such that hemodialysis membrane 138 causes the waste products to pass from an influent side (e.g., a blood side) of hemodialysis membrane 138 to an effluent side (e.g., a dialysate side) of hemodialysis membrane 138. Hemodialysis membrane 138 may be configured to cause the waste products to pass from the blood flow to a dialysate when the waste products pass from the influent side to the effluent side.

Dialyzer 104 includes a dialyzer outlet 139. Dialyzer 104 may support hemodialysis membrane 138 such that dialyzer 104 discharges a blood flow from dialyzer outlet 139 subsequent to hemodialysis membrane 138 causing the waste products to pass from the influent side to the effluent side, such that a substantially cleansed blood flow discharges from dialyzer outlet 139. Dialyzer outlet 139 may be configured to discharge the substantially cleansed blood flow to venous line 112 of medical machine 108.

In examples, dialyzer 104 (e.g., dialyzer body 136) defines a first dialysate access 140 and a second dialysate access 142 in fluid communication with the effluent side of hemodialysis membrane 138. Dialyzer 104 may be configured such that a flow of dialysate enters dialyzer 104 through one of first dialysate access 140 or second dialysate access 142 and exits dialyzer 104 through the other of first dialysate access 140 or second dialysate access 142. Dialyzer 104 may support hemodialysis membrane 138 such that waste products pass to the flow of dialysate when the waste products pass from the influent side of hemodialysis membrane 138 to the effluent side of hemodialysis membrane 138. In examples, first dialysate access 140 is configured to receive and/or discharge dialysate to medical machine 108 via fluid line 117 and second dialysate access 142 is configured to receive and/or discharge dialysate to medical machine 108 via fluid line 119. In some examples, dialyzer 104 is configured to receive a dialysate from medical machine 108 via first dialysate access 140 and discharge the dialysate to medical machine 108 via second dialysate access 142, such that dialyzer 104 enables a cross-current flow exchange as the blood flow within dialyzer 104 flows from filtration assembly 102 to dialyzer outlet 139 and the dialysate flows from first dialysate access 140 to second dialysate access 142.

In some examples, medical machine 108 is configured to receive a spent dialysate from dialysis filter assembly 101 (e.g., via fluid line 117 or fluid line 119) and generate the reinfusion fluid using the spent dialysate. The spent dialysate may be a dialysate discharged from dialyzer 104 via first dialysate access 140 or second dialysate access 142. Medical machine 108 may be configured to substantially purify the spent dialysate received to generate the reinfusion fluid. In examples, medical machine 108 is configured to receive the spent dialysate from dialyzer 104 via fluid line 117 or fluid line 119 and provide the reinfusion fluid generated to filtration assembly 102 via fluid line 121.

Hence, filtration assembly 102 is configured to fluidly communicate with dialyzer 104 when mechanically connected at connecting joint 124 to filter a blood flow received by filtration assembly 102. Filtration assembly 102 is configured to fluidly transfer at least some portion of a blood flow received via filtration proximal access 130 to dialyzer 104 to enable dialyzer 104 to generate a substantially cleansed blood flow. Connecting joint 124 is configured to substantially secure filtration assembly 102 to dialyzer 104, such that filtration assembly 102 and dialyzer 104 behave as a substantially unified body. In examples, connecting joint 124 is configured to mechanically mate filtration assembly 102 with dialyzer 104. Connecting joint 124 may be configured to mechanically mate filtration assembly 102 with a plurality of different types of dialyzers including a connector configured to mate with connecting joint 124, such that a clinician may mechanically mate filtration assembly 102 to a specific dialyzer required for a prescribed hemodialysis treatment of a patient. Dialysis filter assembly 101 may thus be assembled in-situ by a clinician based on the prescribed hemodialysis treatment. Further, configuring filtration assembly 102 and dialyzer 104 to behave as a unified object may ease the set-up and administration of a dialysis treatment by, for example, reducing a number of separate tubing connections, facilitating the securing of filtration assembly 102 and dialyzer 104 to medical machine 108, reducing a number of procedural set-up steps required by a clinician, or other reasons.

Figure 2:
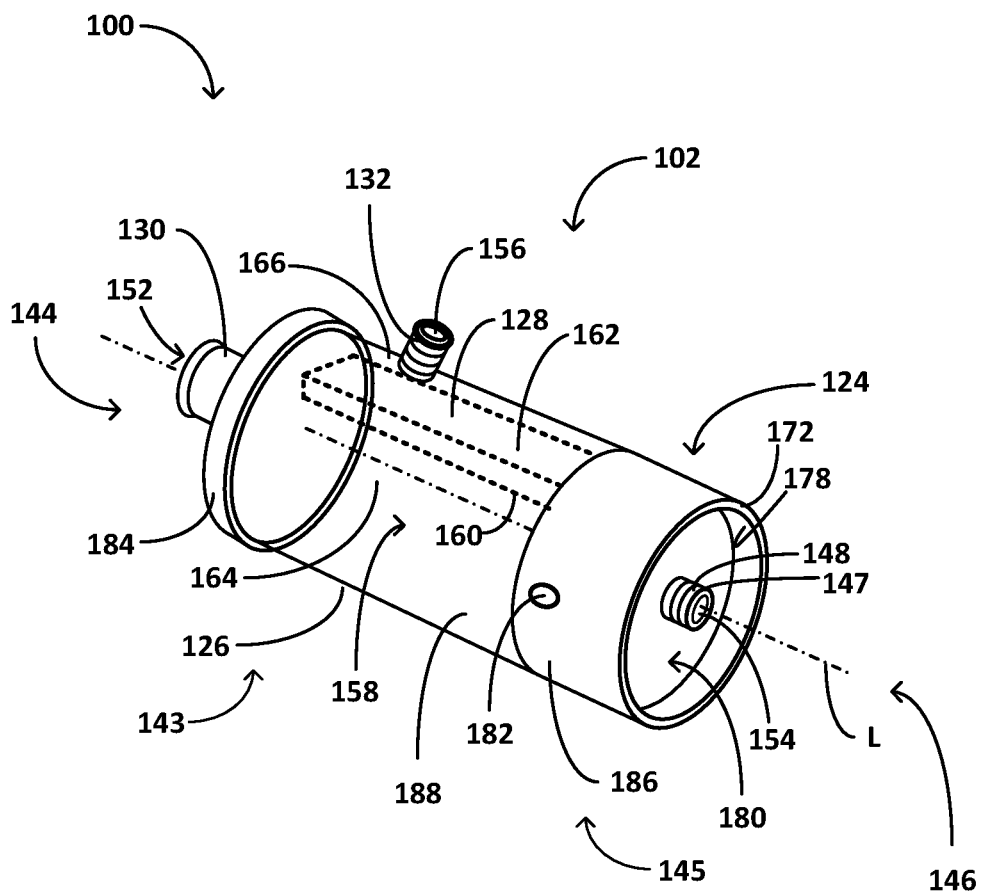
FIG. 2 is a conceptual perspective view of an example filtration assembly of the dialysis filter assembly of FIG. 1.
Figure 3:
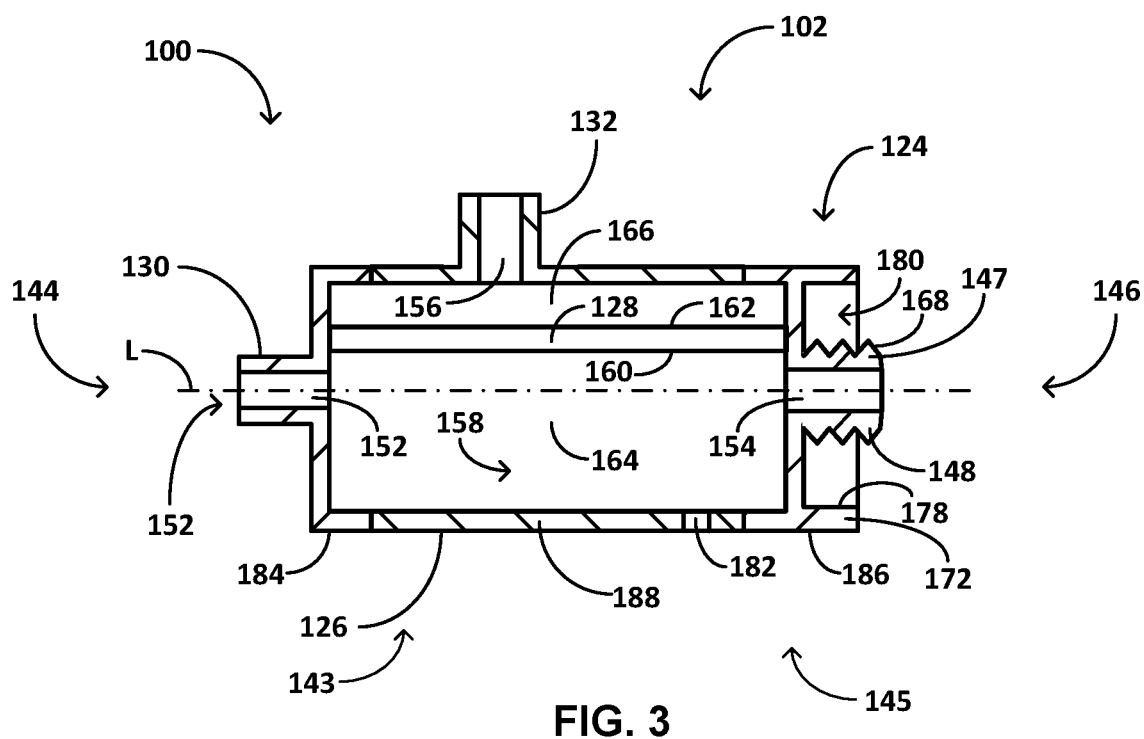
FIG. 3 is a conceptual cross-sectional diagram of the filtration assembly of FIG. 2 with a cutting place taken parallel to the page.
Figure 4:
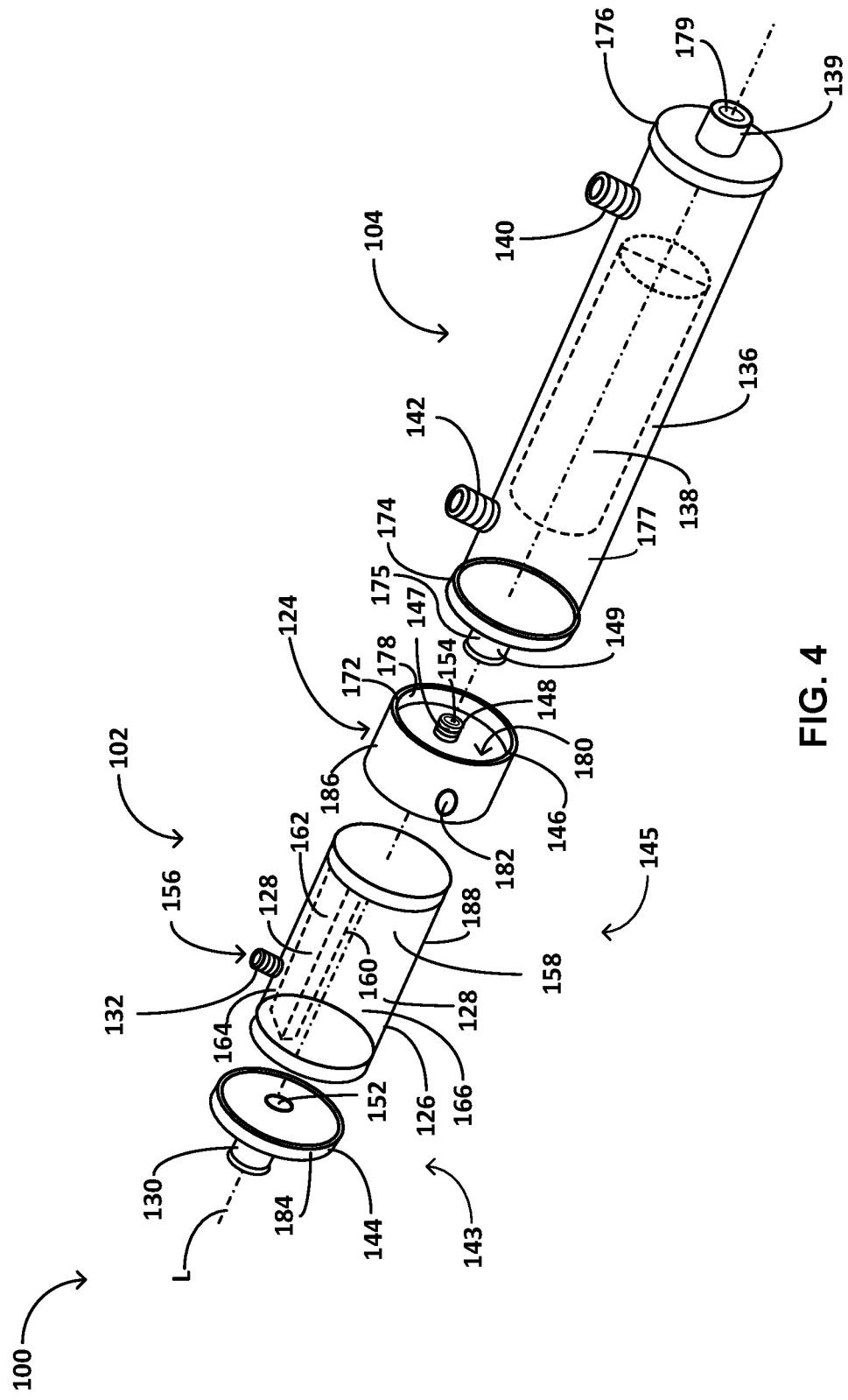
FIG. 4 is a conceptual exploded view of the dialysis filter assembly of FIG. 1, including the filtration assembly of FIG. 2 and FIG. 3.

FIG. 2 illustrates a schematic perspective view of filtration assembly 102 including filtration body 126 supporting filtration membrane 128. Filtration body 126 defines a proximal end 144 ("filtration proximal end 144") and distal end 146 ("filtration distal end 146") opposite filtration proximal end 144. Filtration body 126 may define filtration proximal access 130 at filtration proximal end 144. Filtration assembly 102 defines a longitudinal axis L intersecting filtration proximal end 144 and filtration distal end 146. Filtration body 126 includes a proximal portion 143 ("filtration proximal portion 143") which includes filtration proximal end 144. Filtration body 126 also includes a distal portion 145 ("filtration distal portion 145") which includes filtration distal end 146. FIG. 3 illustrates a schematic cross-sectional view of an filtration assembly 102, with a cutting plane taken parallel to longitudinal axis L. FIG. 4 illustrates a schematic exploded view of dialysis filter assembly 101 including filtration assembly 102 and dialyzer 104.

Filtration body 126 is configured to receive a blood flow (e.g., from arterial line 110 (FIG. 1) and deliver at least a portion of the blood flow to dialyzer 104. Filtration body 126 may be configured to receive the blood flow via filtration proximal access 130. In examples, filtration distal end 146 defines a distal access 148 ("filtration distal access 148") configured to deliver the portion of the blood flow received to dialyzer 104. In some examples, filtration body 126 is configured to receive the blood flow via filtration proximal access 130 and discharge a first portion of the blood flow via filtrate access 132 and a second portion of the blood flow via filtration distal access 148. In some examples, filtration body 126 is configured to receive a blood flow via filtration proximal access 130 and receive a reinfusion fluid via filtrate access 132, and discharge a merged flow comprising the blood flow and the reinfusion fluid via filtration distal access 148.

Filtration body 126 defines an interior volume 158 between filtration proximal end 144 and filtration distal end 146. Filtration proximal access 130 may be in fluid communication with interior volume 158, such that a blood flow may enter filtration assembly 102 via filtration proximal access 130 and enter interior volume 158. Filtration distal access 148 may be in fluid communication with interior volume 158, such that a fluid (e.g., a blood flow) may flow from filtration proximal access 130 to filtration distal access 148 through interior volume 158. Filtrate access 132 may be in fluid communication with interior volume 158, such that a fluid (e.g., a blood flow or reinfusion fluid) may flow between filtration proximal access 130 and filtrate access 132 through interior volume 158.

Filtration proximal access 130 may define a fluid passage 152 configured to allow a fluid to flow through filtration proximal access 130 to and/or from interior volume 158. Filtration distal access 148 may define a fluid passage 154 configured to allow a fluid to flow through filtration distal access 148 to and/or from interior volume 158. Filtrate access 132 may define a fluid passage 156 configured to allow a fluid to flow through filtrate access 132 to and/or from interior volume 158.

Filtration body 126 is configured to mechanically support filtration membrane 128 within interior volume 158. Filtration membrane 128 may be configured to cause an alteration in a composition, concentration, or some other fluid property of a blood flow as the blood flow passes from filtration proximal access 130 to filtration distal access 148. For example, filtration membrane 128 may be configured to remove an aqueous solution comprising uremic toxins from a blood flow as the blood flow passes from filtration proximal access 130 to filtration distal access 148. Filtration body 126 may be configured to cause the aqueous solution to discharge via filtrate access 132. Filtration membrane 128 may be configured to cause a reinfusion fluid to inject into a blood flow as the blood flow passes from filtration proximal access 130 to filtration distal access 148. Filtration body 126 may be configured to receive the reinfusion fluid via filtrate access 132. In examples, filtration membrane 128 is configured to enable a fluid (e.g., some portion of a blood flow and/or a reinfusion fluid) to pass through filtration membrane 128 to cause the alteration in composition, concentration, or some other fluid property of the blood flow passing from filtration proximal access 130 to filtration distal access 148.

Filtration body 126 is configured to discharge a blood flow from filtration distal access 148 to dialyzer 104 (FIG. 1). Filtration body 126 is configured to removably mechanically connect to dialyzer 104 through connecting joint 124. In examples, connecting joint 124 is configured such that filtration distal access 148 is in fluid communication with dialyzer 104 when connecting joint 124 connects filtration body 126 and dialyzer 104 such that, for example, filtration assembly 102 may deliver the portion of the blood flow received via filtration proximal access 130 to dialyzer 104. Connecting joint 124 may be configured such that filtration body 126 substantially behaves as a unified object with dialyzer 104 when connecting joint 124 mechanically connects filtration body 126 and dialyzer 104. In examples, connecting joint 124 is configured to connect filtration body 126 and dialyzer body 136 such that filtration body 126 remains substantially stationary relative to dialyzer body 136, and vice-versa, when a force is exerted on filtration body 126 and/or the dialyzer body.

Filtration body 126 includes a filtration body connector 147 configured to enable the mechanical connection between filtration body 126 and dialyzer 104. Filtration body connector 147 may be a portion of or otherwise secured to connecting joint 124. Filtration body connector 147 may be configured to mechanically mate with dialyzer body 136 to enable the connection between filtration body 126 and dialyzer 104. For example, filtration body connector may be configured to mechanically mate with a dialyzer body connector 149 defined by dialyzer 104 (FIG. 4). In examples, filtration body connector 147 is configured such that a clinician may mechanically mate filtration body 126 with dialyzer body 136, such that the clinician may cause the connection of filtration assembly 102 and dialyzer 104 at a treatment site in preparation for delivery of a prescribed hemodialysis treatment to patient 106. In examples, filtration body connector 147 is configured to mechanically mate with dialyzer body 136 (e.g., dialyzer body connector 149) when filtration body 126 and dialyzer body 136 are manipulated by hand (e.g., using hand force only), such that filtration body 126 and dialyzer body 136 may be connected in a manner not requiring an assembly tool. For example, filtration body connector 147 may be configured to threadably engage dialyzer body 136 to enable the connection. As another example, filtration body connector 147 may be configured to form a snap-fit with dialyzer body 146 to enable the connection. Filtration body connector 147 may be mechanically mate with dialyzer body 146 in any manner sufficient to cause filtration body 126 to remain substantially stationary relative to dialyzer body 136, and vice-versa.

Filtration body connector 147 may be configured to transmit a force from filtration body 126 to dialyzer body 136 or from dialyzer body 136 to filtration body 126 when filtration body connector 147 mechanically mates filtration body 126 and dialyzer body 136. In examples, filtration body connector 147 is configured to cause filtration body 126 and dialyzer body 136 to generate an action-reaction force pair, so that when filtration body 126 exerts an action force on dialyzer 104, dialyzer 104 exerts an oppositely oriented reaction force on filtration body 126, and vice-versa. Filtration body connector 147 may be configured such that the action-reaction force pair causes filtration body 126 and dialyzer body 136 to act as a substantially unified body when a force is exerted on filtration body 126 and/or dialyzer body 136.

In examples, filtration body connector 147 includes a bearing structure configured to transmit a force from filtration body 126 to dialyzer body 136 or from dialyzer body 136 to filtration body 126 when filtration body connector 147 mechanically mates filtration assembly 102 and dialyzer 104. The bearing structure may be configured to mechanically engage dialyzer body 136 (e.g., dialyzer body connector 149) to cause filtration body 126 and dialyzer body 136 to generate an action-reaction force pair. In examples, the bearing structure is configured to at least transmit a force acting in a direction parallel to longitudinal axis L when filtration body connector 147 mechanically mates filtration body 126 and dialyzer body 136 and longitudinal axis L extends through filtration body 126 and dialyzer body 136.

In some examples, filtration body connector 147 defines a screw thread 168 (FIG. 3), and a flank surface extending between a thread root and a thread crest of screw thread 168 defines the bearing structure. Screw thread 168 may be configured to engage with a screw thread defined by dialyzer body 136 (e.g., dialyzer body connector 149) when filtration body connector 147 mechanically mates filtration body 126 and dialyzer body 136. In examples, screw thread 168 is an external screw thread configured to threadably engage an internal screw thread (e.g., an internal screw thread defined by dialyzer body 136). In other examples, screw thread 168 is an internal screw thread configured to threadably engage an external screw thread (e.g., an external screw thread defined by dialyzer body 136). In examples, screw thread 168 is configured to threadably engage with a screw thread defined by dialyzer body 136 when filtration body connector 147 mechanically mates filtration body 126 and dialyzer body 136.

In some examples, filtration body connector 147 defines a flange and a flange face defines the bearing surface. The flange face may be configured to mechanically engage with a structure (e.g., a pin, another flange, and/or other structure) defined by dialyzer 104 (e.g., dialyzer body connector 149) when filtration body connector 147 mechanically mates filtration body 126 and dialyzer body 136. In some examples, filtration body connector 147 defines a pin slot and a slot face defining the bearing surface. The pin slot may be configured to receive a pin defined by dialyzer 104 when filtration body connector 147 mechanically mates filtration body 126 and dialyzer body 136. In some examples, filtration body connector 147 defines a pin configured to mechanically engage a pin slot or other structure defined by dialyzer body 136.

Filtration body connector 147 may be configured to mechanically connect filtration body 126 and dialyzer body 136 when filtration body 126 contacts dialyzer body 136 and experiences a motion relative to dialyzer body 136. For example, filtration body connector 147 may be configured to mechanically connect filtration body 126 and dialyzer body 136 when filtration body 126 is placed in contact with dialyzer body 136 and rotated around longitudinal axis L relative to dialyzer body 136. As another example, filtration body connector 147 may be configured to mechanically connect filtration body 126 and dialyzer body 136 when filtration body 126 is placed in contact with dialyzer body 136 and displaced in a direction toward dialyzer body 136, or vice-versa. Filtration body connector 147 may be configured such that a clinician may manipulate filtration body 126 and/or dialyzer body 136 to produce the relative motion, such that the clinician may cause filtration body connector 147 to mechanically mate filtration body 126 and/or dialyzer body 136.

In some examples, filtration body 126 defines a guiding structure 172 configured to mechanically engage dialyzer body 136 in addition to the mechanical engagement caused by filtration body connector 147. Filtration body 126 may be configured to limit movement of filtration body 126 and/or dialyzer body 136 when guiding structure 172 mechanically engages dialyzer body 136. For example, guiding structure 172 may be configured to cause dialyzer body 136 to substantially align with filtration body 126 to facilitate mechanical mating of filtration body 126 and dialyzer body 136 using filtration body connector 147. Guiding structure 172 may be configured to limit motion a displacement of dialyzer body 136 in a direction away (e.g., traverse to) from longitudinal axis L to facilitate mechanical mating of filtration body 126 and dialyzer body 136 using filtration body connector 147. For example, guiding structure 172 may be configured such that, when guiding structure 172 mechanically engages a proximal portion 174 of dialyzer body 136 ("dialyzer proximal portion 174") (FIG. 4), guiding structure 172 aligns dialyzer 104 to cause longitudinal axis L to intersect both dialyzer proximal portion 174 and a distal portion 176 of dialyzer body 136 ("dialyzer distal portion 176") (FIG. 4).

In some examples, guiding structure 172 defines a guiding surface 178 configured to mechanically engage dialyzer proximal portion 174 to cause dialyzer body 136 to substantially align with filtration body 126. Guiding surface 178 may be configured to slidably contact dialyzer proximal portion 174 to mechanically engage dialyzer proximal portion 174. In examples, guiding surface 178 is configured to slidably contact dialyzer proximal portion 174 as dialyzer proximal portion 174 translates substantially parallel to and/or rotates around longitudinal axis L as, for example, filtration body connector 147 mechanically mates filtration body 126 and dialyzer body 136. In some examples, as depicted in FIGS. 2 and 3, guiding surface 178 is configured on guiding structure 172 such that guiding surface 178 substantially faces in a direction toward longitudinal axis L. In other examples, guiding surface 178 may be configured on guiding structure 172 such that guiding surface 178 substantially faces in a direction away from longitudinal axis L, or has some other orientation with respect to longitudinal axis L. In some examples, guiding surface 178 surrounds at least some portion of filtration body connector 147. Guiding surface 178 may be configured to surround at least some portion of filtration body connector 147 and dialyzer body connector 149 when filtration body connector 147 mechanically mates with dialyzer body connector 149.

Filtration body 126 may define a recess 180 ("filtration body recess 180") configured to receive some portion of dialyzer 104 when filtration body connector 147 mechanically mates filtration body 126 and dialyzer body 136. For example, filtration body recess 180 may be configured to receive some portion of dialyzer proximal portion 174 when filtration body connector 147 mechanically mates filtration body 126 and dialyzer body 136. In examples, connecting joint 124 defines filtration body recess 180. Filtration body recess 180 may be configured to surround some portion of or substantially all of a circumference (e.g., a circumference around longitudinal axis L) defined by dialyzer distal portion 176 when filtration body connector 147 mechanically mates filtration body 126 and dialyzer body 136. In examples, guiding surface 178 defines some portion of filtration body recess 170.

In some examples, filtration body 126 may define a protrusion (not shown) configured to insert into a dialyzer recess defined by dialyzer 104 when filtration body connector 147 mechanically mates filtration body 126 and dialyzer body 136. The protrusion of filtration body 126 may be configured to insert into the dialyzer recess when filtration body connector 147 mechanically mates filtration body 126 and dialyzer body 136. In examples, connecting joint 124 defines the protrusion of filtration body 126. The protrusion of filtration body 126 may be configured to surround some portion of or substantially all of a circumference (e.g., a circumference around longitudinal axis L) defined by dialyzer distal portion 176 when filtration body connector 147 mechanically mates filtration body 126 and dialyzer body 136. In examples, guiding surface 178 defines some portion of the protrusion of filtration body 126.

Hence, filtration assembly 102 may be configured to fluidly transfer at least some portion of a blood flow received via filtration proximal access 130 to dialyzer 104. Filtration body connector 147 may be configured to removably secure filtration assembly 102 to dialyzer 104, such that filtration assembly 102 and dialyzer 104 behave as a substantially unified body. Filtration body connector 147 may be configured to mechanically mate filtration assembly 102 to dialyzer 104. In examples, filtration body connector 147 is configured such that a clinician may mechanically mate filtration assembly 102 and dialyzer 104 through manual manipulation by the clinician, such that dialysis filter assembly 101 may be assembled on-site by a clinician based on a prescribed hemodialysis treatment. The removable connection provided by connector 147 also enables a clinician (or other user) to disconnect filtration assembly 102 and dialyzer 104, e.g., to replace dialyzer 104 with a different dialyzer or for other reasons.

As discussed, filtration body 126 may be configured to mechanically support filtration membrane 128 within interior volume 158. In examples, filtration body 126 mechanically supports filtration membrane 128 to cause filtration membrane 128 to convect an aqueous solution containing waste products from a blood flow entering filtration proximal access 130. Filtration body 126 may mechanically support filtration membrane 128 to cause a first portion of the blood flow comprising the aqueous solution to pass through filtration membrane 128 as discharge through filtrate access 132 as a second portion of the blood flow passes from filtration proximal access 130 to filtration distal access 148. In examples, filtration body 126 mechanically supports filtration membrane 128 to cause filtration membrane 128 to issue a reinfusion fluid received via filtrate access 132 into a blood flow entering filtration proximal access 130. Filtration body 126 may mechanically support filtration membrane 128 to cause the issued reinfusion fluid and the blood flow to merge, such that filtration body 126 provides the merged flow to filtration distal access 148. In some examples, filtration body 126 defines a filtration inlet 182 in fluid communication with interior volume 158. Filtration body 126 may be configured to receive a reinfusion fluid via filtration inlet 182 (e.g., from medical machine 108 (FIG. 1) and cause the reinfusion fluid and the blood flow to merge. In some examples, filtration body 126 is configured to discharge the first portion of the blood flow through filtrate access 132 (e.g., to medical machine 108) and receive a reinfusion fluid (e.g., from medical machine 108) through filtration inlet 182.

Filtration membrane 128 may define a first side 160 ("filter first side 160") and a second side 162 ("filter second side 162") opposite filter first side 160. Filtration membrane 128 may be configured to allow a fluid to pass between filter first side 160 and filter second side 162. In examples, filtration membrane 128 may be configured to preferentially allow one or more substances within a fluid to pass between filter first side 160 and filter second side 162. Filtration membrane 128 may be configured to limit and/or substantially prevent other substances within the fluid from passing between filter first side 160 and filter second side 162. In some examples, filtration membrane 128 is configured to preferentially allow an aqueous solution of uremic toxins to pass from filter first side 160 to filter second side 162 when a blood flow comprising the aqueous solution of uremic toxins is in contact with filter first side 160, such that filtration membrane 128 acts to remove the solution of uremic toxins from the blood flow contacting filter first side 160. In some examples, filtration membrane 128 is configured to preferentially allow a reinfusion fluid to pass from filter second side 162 to filter first side 160 while tending to limit and/or substantially prevent certain substances (e.g., microbial substances) from passing from filter second side 162 to filter first side 160, such that filtration membrane 128 acts to remove the certain substances from the reinfusion fluid passing through filtration membrane 128.

Filtration body 126 may mechanically support filtration membrane 128 such that filtration proximal access 130, filtration distal access 148, and/or filtrate access 132 are in fluid communication with filtration membrane 128. In examples, filtration body 126 mechanically supports filtration membrane 128 within interior volume 158 such that filtration membrane 128 substantially separates (e.g., fully separates or nearly fully separates to the extent permitted by manufacturing tolerances) filtration proximal access 130 and filtrate access 132, so that, for example, at least some portion of a fluid flowing between filtration proximal access 130 and filtrate access 132 passes through filtration membrane 128. Filtration body 126 may mechanically support filtration membrane 128 within interior volume 158 such that filtration membrane 128 substantially separates filtration distal access 148 and filtrate access 132, so that, for example at least some portion of a fluid flowing between filtration distal access 148 and filtrate access 132 passes through filtration membrane 128.

In some examples, filtration body 126 also mechanically supports filtration membrane 128 within interior volume such a fluid may flow between filtration proximal access 130 and filtration distal access 148 without passing through filtration membrane 128. Hence, filtration body 126 may mechanically support filtration membrane such that a fluid flow from filtration proximal access 130 to filtrate access 132 or a fluid flow from filtrate access 132 to filtration distal access 148 passes through filtration membrane 128, while a fluid flow from filtration proximal access 130 to filtration distal access 148 may not pass through filtration membrane 128.

In some examples, filtration body 126 mechanically supports filtration membrane 128 to separate interior volume 158 into a first portion 164 ("first volume portion 164") and a second portion 166 ("second volume portion 166"). Filtration membrane 128 may be configured such a fluid exchanged between first volume portion 164 and second volume portion 166 passes through filtration membrane 128. In examples, filter first side 160 defines a boundary of first volume portion 164. Filter second side 162 may define a boundary of second volume portion 166. In examples, filtration body 126 mechanically supports filtration membrane 128 such that a fluid flowing between filtration proximal access 130 and filtration distal access 148 may pass through first volume portion 164 while substantially avoiding second volume portion 166. Filtration body 126 may mechanically support filtration membrane 128 such that a fluid flowing between filtrate access 132 and filtration proximal access 130 or filtration distal access 148 passes between second volume portion 166 and first volume portion 164.

Filtration membrane 128 may have any suitable configuration. In some examples, filtration member includes a tubular shaped membrane defining a flow passage through an interior of the tubes. Filtration membrane 128 may include a membrane wall defining and interior surface facing toward the flow passage and an exterior surface opposite the interior surface. Filtration membrane 128 may be configured to allow a fluid to flow between the interior surface and the exterior surface. In examples, filter first side 160 is one of the interior surface or the exterior surface and filter second side 162 is the other of the interior surface or the exterior surface. In some examples, filtration membrane 128 may include a plurality of tubular shaped membranes. Filter first side 160 may include a plurality of interior surfaces or a plurality of exterior surfaces defined by the plurality of tubular shaped membranes. Filter second side 162 may include a plurality of interior surfaces (e.g., when filter first side 160 includes the plurality of exterior surfaces) or a plurality of exterior surfaces (e.g., when filter first side 160 includes the plurality of interior surfaces) defined by the plurality of tubular shaped membranes. In other examples, filtration membrane is a substantially flat or curved body defining filter first side 160 on a first defined surface and defining filter second side 162 on a second defined surface opposite the first defined surface.

Filtration body 126 may include a proximal cap 184, a distal cap 186, and a wall 188 ("filtration body wall 188") extending between proximal cap 184 and distal cap 186. Filtration proximal access 130 may be attached to proximal cap 184. In examples, proximal cap 184 defines filtration proximal access 130. Filtration distal access 148 may be attached to or defined by distal cap 186. Filtrate access 132 may be attached to or defined by filtration body wall 188. Fluid passage 152 may be configured to provide a flow path through proximal cap 184 to interior volume 158. Fluid passage 154 may be configured to provide a flow path through distal cap 186 to interior volume 158. Fluid passage 156 may be configured to provide a flow path through filtration body wall 188 to interior volume 158. In examples, proximal cap 184 is secured to filtration body wall 188 such that proximal cap 184 and filtration body wall 188 are substantially stationary with respect to each other. Distal cap 186 may be secured to filtration body wall 188 such that distal cap 186 and filtration body wall 188 are substantially stationary with respect to each other. In some examples, proximal cap 184, distal cap 186, and filtration body wall 188 are secured to a portion of filtration body 126, such that proximal cap 184, distal cap 186, and filtration body wall 188 act as a substantially unified body.

Figure 5:
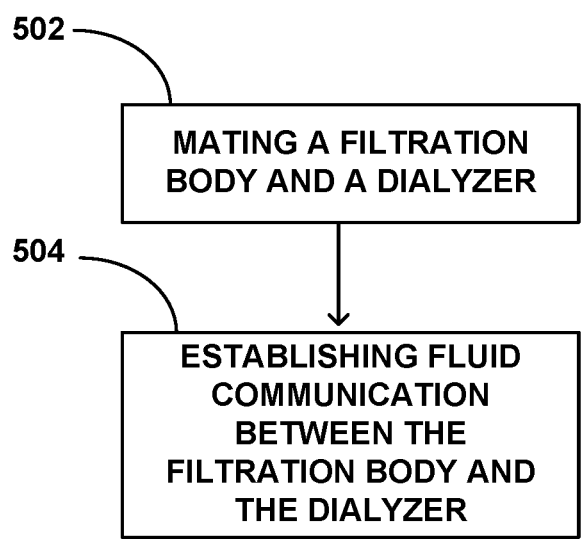
FIG. 5 is a flow diagram of an example technique of using the filtration assembly of FIGS. 1-4.

A technique for connecting filtration assembly 102 and dialyzer 104 is illustrated in FIG. 5. Although the technique is described mainly with reference to filtration assembly 102 of FIGS. 1-4, the technique may be applied to other filtration assemblies configured to removably mechanically connect to a dialyzer in other examples.

The technique includes mechanically mating filtration body 126 and dialyzer 104 (502). Filtration body 126 may removably mechanically mate to dialyzer 104. Filtration body 126 may mechanically mate with dialyzer body 136 to mechanically mate filtration body 126 and dialyzer 104. Filtration body 126 may experience motion relative to dialyzer 104 to when filtration body 126 mechanically mates with dialyzer 104. In examples, filtration body 126 rotates around longitudinal axis L to mechanically mate with dialyzer 104. In examples, filtration body 126 displaces toward dialyzer 104 to mechanically mate with dialyzer 104. The mechanical mating of filtration body 126 and dialyzer 104 may secure filtration body 126 to dialyzer 104, such that filtration body 126 is substantially stationary relative to dialyzer body 136.

Filtration body connector 147 may mechanically mate with dialyzer 104 to cause filtration body 126 to mechanically mate with dialyzer 104. In examples, filtration body connector 147 mechanically mates with dialyzer body connector 149. A bearing structure of filtration body 126 may mechanically engage dialyzer 104 when filtration body 126 and dialyzer 104 mechanically mate. The bearing structure may transmit a force from filtration body 126 to dialyzer 104 or from dialyzer 104 to filtration body 126 when the bearing structure mechanically engages dialyzer 104. In examples, filtration body connector 147 threadably engages dialyzer 104 to mechanically mate with dialyzer 104. In examples, a flange and/or a pin defined by filtration body 126 mechanically engages dialyzer 104 to mechanically mate with dialyzer 104.

Filtration body 126 and dialyzer body 136 may align when filtration body 126 mechanically mates with dialyzer 104. Guiding structure 172 may mechanically engage dialyzer proximal portion 174 to the alignment. Guiding surface 178 defined by guiding structure 172 may slidably contact dialyzer proximal portion 174 as filtration body connector 147 mechanically mates filtration body 126 and dialyzer 104. In examples, guiding surface 178 surrounds at least some portion of filtration body connector 147 and dialyzer body connector 149 when filtration body 126 mechanically mates with dialyzer 104. In some examples, recess 180 of filtration body 126 receives some portion of dialyzer proximal portion 174 when filtration body 126 mechanically mates with dialyzer 104. In some examples, a protrusion of filtration body 126 inserts into a recess defined by dialyzer proximal portion 174 when filtration body 126 mechanically mates with dialyzer 104.

Filtration body 126 establishes fluid communication with dialyzer 104 when filtration body connector 147 properly mechanically mates with dialyzer 104 (504). Filtration body 126 may establish fluid communication with dialyzer 104 using filtration distal access 148. In examples, filtration body 126 establishes fluid communication between filtration proximal access 130 and dialyzer 104 using filtration distal access 148. Filtration proximal access 130 and filtration distal access 148 may fluidly communicate through interior volume 158 defined by filtration body 126. In examples, dialyzer proximal portion 174 includes a dialyzer proximal access 175 configured to establish fluid communication 104 with filtration distal access 148. Dialyzer proximal access 175 may be configured to be in fluid communication with a dialyzer interior volume 177 defined by dialyzer body 136. Dialyzer body 136 may be configured to mechanically support hemodialysis membrane 138 within dialyzer interior volume 177. In examples, dialyzer distal portion 176 includes a dialyzer distal access 179 in fluid communication with dialyzer interior volume 177 and/or filtration distal access 148.

Filtration proximal access 130 and filtration distal access 148 may fluidly communicate with filtrate access 132 through interior volume 158 as filtration body 126 fluidly communicates with dialyzer 104. Filtration proximal access 130 may fluidly communicate with filtrate access 132 through filtration membrane 128 separating filtration proximal access 130 and filtrate access 132. Filtration distal access 148 may fluidly communicate with filtrate access 132 through filtration membrane 128 separating filtration distal access 148 and filtrate access 132.

In examples, filtration body 126 receives a blood flow via filtration proximal access 130. Filtration proximal access 130 may receive the blood flow from arterial line 110 of medical machine 108. Filtration body 126 may provide a first portion of the blood flow to filtrate access 132 and a second portion of the blood flow to filtration distal access 148. Filtration body 126 may mechanically support filtration membrane 128 such that the first portion of the blood flow passes from filter first side 160 to filter second side 162 of filtration membrane 128. Filtrate access 132 may provide the second portion of the blood flow to medical machine 108. In examples, filtration body 126 receives a blood flow via filtration proximal access 130 and receives a reinfusion fluid via filtrate access 132. Filtration body 126 may provide a merged flow including the blood flow and the reinfusion fluid to filtration distal access 148. Filtration body 126 may mechanically support filtration membrane 128 such that the reinfusion fluid passes from a filter second side 162 to filter first side 160. Filtrate access 132 may receive the reinfusion fluid from medical machine 108.

Dialyzer 104 may receive a blood flow from filtration distal access 148 when filtration body 126 establishes fluid communication with dialyzer 104. Dialyzer 104 may mechanically support hemodialysis membrane 138. Dialyzer 104 may use hemodialysis membrane 138 to convect and/or diffuse waste products from the influent side of hemodialysis membrane 138 to effluent side of hemodialysis membrane 138. Hemodialysis membrane 138 may pass the waste products to a dialysate when the waste products pass from the influent side to the effluent side. Dialyzer 104 may receive the dialysate (e.g., from medical machine 108) through one of first dialysate access 140 or second dialysate access 142 and discharge the dialysate through the other of first dialysate access 140 or second dialysate access 142. Dialyzer 104 may discharge a cleansed blood flow through dialyzer outlet 139 subsequent to hemodialysis membrane 138 causing the waste products to pass from the influent side to the effluent side, Dialyzer outlet 139 may discharge the substantially cleansed blood flow to venous line 112 of medical machine 108.

The disclosure includes the following examples.

Example 1: A medical system comprising: a filtration membrane including a first side and a second side; and a filtration body defining an interior volume between a proximal end and a distal end, wherein the filtration membrane is positioned within the interior volume, the filtration body comprising: a filtration proximal access at the proximal end configured to receive a blood flow, wherein the filtration proximal access is in fluid communication with the first side of the filtration membrane; a filtrate access in fluid communication with the second side of the filtration membrane; a filtration distal access at the distal end, wherein the filtration distal access is in fluid communication with the first side of the filtration membrane and the filtration proximal access, wherein the filtration distal access is configured to provide at least a portion of the blood flow to a dialyzer; and a filtration body connector secured to the distal end, wherein the filtration body connector is configured to removably mechanically mate with the dialyzer to enable the filtration distal access to provide the portion of the blood flow to the dialyzer.

Example 2: The medical system of example 1, wherein the filtration membrane is positioned within the interior volume to cause a first portion of the blood flow to pass from the first side of the filtration membrane to the second side of the filtration membrane when the first portion flows from the filtration proximal access to the filtrate access, wherein the first portion includes an aqueous solution of a uremic toxin, and wherein the filtration membrane is positioned within the interior volume to cause a second portion of the blood flow to flow from the filtration proximal access to the dialyzer when the filtration body connector is mechanically mated with the dialyzer.

Example 3: The medical system of example 1 or example 2, wherein the filtration membrane is positioned within the interior volume to cause a reinfusion fluid received by the filtrate access to pass from the second side of the filtration membrane to the first side of the filtration membrane when the reinfusion fluid flows from the filtrate access to the filtration distal access, and wherein the filtration membrane is positioned within the interior volume to cause a merged flow including the blood flow and the reinfusion fluid to flow from the first side to the dialyzer.

Example 4: The medical system of any of examples 1-3, wherein the filtration proximal access is configured to receive the blood flow from an arterial line of a dialysis machine configured to receive the blood flow from a patient.

Example 5: The medical system of any of examples 1-4, wherein the filtrate access is configured to discharge a first portion of the blood flow to a dialysis machine configured to receive the first portion of the blood flow and generate a reinfusion fluid using the first portion of the blood flow for delivery to a patient.

Example 6: The medical system of any of examples 1-5, wherein the filtration body comprises a filtration inlet configured to receive a reinfusion fluid, wherein the reinfusion access is in fluid communication with the filtration distal access and the first side of the filtration membrane.

Example 7: The medical system of any of examples 1-6, wherein the filtration body connector includes a bearing structure configured to transmit a force from the filtration body to the dialyzer or from the dialyzer to the filtration body when the filtration body connector mechanically mates with the dialyzer.

Example 8: The medical system of any of examples 1-7, wherein the filtration body connector is configured to mechanically mate with the dialyzer when the filtration body is rotated relative to the dialyzer.

Example 9: The medical system of any of examples 1-8, wherein the filtration body connector is configured to mechanically mate with the dialyzer when the filtration body is displaced in a direction toward the dialyzer or the dialyzer is displaced in a direction toward the filtration body.

Example 10: The medical system of any of examples 1-9, wherein the filtration body defines a recess configured to receive a protrusion of the dialyzer when the filtration body connector mechanically mates with the dialyzer, and wherein the filtration body connector is defined within the recess.

Example 11: The medical system of any of examples 1-10, wherein the filtration body defines a protrusion configured to insert into a recess of the dialyzer when the filtration body connector mechanically mates with the dialyzer, and wherein the filtration body connector is defined on the protrusion.

Example 12: The medical system of any of examples 1-11, wherein the filtration body includes: a proximal cap at the proximal end; a distal cap at the distal end; and a wall extending from the proximal cap to the and distal cap, wherein the proximal cap defines the filtration proximal access, the distal cap defines the filtration distal access, and the wall defines the filtrate access.

Example 13: The medical system of any of examples 1-12, further comprising the dialyzer, wherein the dialyzer includes a dialyzer body defining a dialyzer body connector, and wherein the dialyzer body connector is configured to mechanically mate with the filtration body connector to cause the filtration body connector to mechanically mate with the dialyzer.

Example 14: The medical system of example 13, wherein the dialyzer comprises a hemodialysis membrane including a blood flow side and a dialysate side; wherein the dialyzer body defines a dialyzer interior volume, wherein the hemodialysis membrane is positioned within the dialyzer interior volume, the dialyzer body comprising: a dialyzer proximal access configured to receive a conditioned blood flow from the filtration body when the filtration body connector mechanically mates with the dialyzer body connector, wherein the dialyzer proximal access is in fluid communication with the blood flow side; a dialyzer distal access in fluid communication with the blood flow side and the dialyzer proximal access; a dialyzer inlet configured to receive dialysate from a dialysis machine, wherein the dialyzer inlet is in fluid communication with the dialysate side; and a dialyzer outlet in fluid communication with the dialysate side and the dialyzer inlet.

Example 15: The medical system of example 14, wherein the hemodialysis membrane is configured to diffuse a uremic toxin from the blood side to the dialysate side when the conditioned blood flow contacts the blood flow side and the dialysate contacts the dialysate side.

Example 16: A medical system comprising: a filtration membrane including a first side and a second side; and a filtration body defining an interior volume between a proximal end and a distal end, wherein the filtration membrane is positioned within the interior volume, the filtration body comprising: a proximal cap at the proximal end defining a filtration proximal access configured to receive a blood flow, wherein the filtration proximal access is in fluid communication with the first side of the filtration membrane; a filtrate access in fluid communication with the second side of the filtration membrane; a distal cap at the distal end defining a filtration distal access, wherein the filtration distal access is in fluid communication with the first side of the filtration membrane and the filtration proximal access, wherein the filtration distal access is configured to provide at least a portion of the blood flow to a dialyzer; and a filtration body connector secured to the distal cap, wherein the filtration body connector is configured to removably mechanically mate with the dialyzer to enable the filtration distal access to provide the portion of the blood flow to the dialyzer.

Example 17: The medical system of example 16, further comprising the dialyzer, wherein the dialyzer comprises: a hemodialysis membrane including a blood flow side and a dialysate side, wherein the hemodialysis membrane is configured to diffuse a uremic toxin from the blood side to the dialysate side when a stream of blood contacts the blood flow side and a dialysate contacts the dialysate side; and a dialyzer body defining a dialyzer interior volume, wherein the hemodialysis membrane is positioned within the dialyzer interior volume, the dialyzer body comprising: a dialyzer body connector secured to the dialyzer proximal end, wherein the dialyzer body connector is configured to mechanically mate with the filtration body connector to cause the filtration body connector to mechanically mate with the dialyzer; a dialyzer proximal access configured to receive the stream of blood from the filtration body when the filtration body connector mechanically mates with the dialyzer body connector, wherein the dialyzer proximal access is in fluid communication with the blood flow side; a dialyzer distal access in fluid communication with the blood flow side and the dialyzer proximal access; a dialyzer inlet configured to receive the dialysate from a dialysis machine, wherein the dialyzer inlet is in fluid communication with the dialysate side; and a dialyzer outlet in fluid communication with the dialysate side and the dialyzer inlet.

Example 18: The medical system of example 16 or example 17, wherein the filtration body connector includes a bearing structure configured to transmit a force from the filtration body to the dialyzer or from the dialyzer to the filtration body when the filtration body connector mechanically mates with the dialyzer.

Example 19: A method, comprising: mechanically mating a filtration body connector secured to a distal end of a filtration body with a dialyzer, wherein the mechanical mating is a removable mechanical mating, wherein the filtration body defines an filtration proximal access at a proximal end of the filtration body in fluid communication with an first side of a filtration membrane, a filtrate access in fluid communication with a second side of the filtration membrane, and a filtration distal access in fluid communication with the filtration proximal access and the first side of the filtration membrane; and establishing fluid communication between the filtration distal access and the dialyzer when the filtration body connector mechanically mates with the dialyzer.

Example 20: The method of example 19, wherein mechanically mating the filtration body connector with the dialyzer comprises inserting a protrusion into a recess, wherein one of the filtration body or the dialyzer defines the protrusion and the other of the filtration body or the dialyzer defines the recess.

Various examples of the disclosure have been described. Any combination of the described systems, operations, or functions is contemplated. These and other examples are within the scope of the following claims.

What is claimed is:
1. A medical system comprising:
a filtration membrane including a first side and a second side; and
a filtration body defining an interior volume between a proximal end and a distal end, wherein the filtration membrane is positioned within the interior volume, the filtration body comprising:
a filtration proximal access at the proximal end configured to receive a blood flow, wherein the filtration proximal access is in fluid communication with the first side of the filtration membrane;
a filtrate access in fluid communication with the second side of the filtration membrane;
a filtration distal access at the distal end,
wherein the filtration distal access is in fluid communication with the first side of the filtration membrane and the filtration proximal access, wherein the filtration distal access is configured to provide at least a portion of the blood flow to a dialyzer; and
a filtration body connector secured to the distal end, wherein the filtration body connector is configured to removably mechanically mate with the dialyzer to enable the filtration distal access to provide the portion of the blood flow to the dialyzer when the filtration body connector mechanically mates with the dialyzer; and
the dialyzer,
wherein the dialyzer includes a dialyzer body,
wherein the filtration body defines one of a protrusion or a recess and the dialyzer body defines the other of the protrusion or the recess,
wherein the recess is configured to receive the protrusion,
wherein the protrusion or the recess defined by the filtration body defines the filtration distal access and defines the filtration body connector,
wherein the protrusion or the recess defined by the dialyzer body defines a dialyzer body connector, and
wherein the dialyzer body connector is configured to removably mechanically mate with the filtration body connector to cause the filtration body connector to removably mechanically mate with the dialyzer.

2. The medical system of claim 1,
wherein the filtration membrane is positioned within the interior volume to cause a first portion of the blood flow to pass from the first side of the filtration membrane to the second side of the filtration membrane when the first portion flows from the filtration proximal access to the filtrate access, wherein the first portion includes an aqueous solution of a uremic toxin, and
wherein the filtration membrane is positioned within the interior volume to cause a second portion of the blood flow to flow from the filtration proximal access to the dialyzer when the filtration body connector is mechanically mated with the dialyzer.

3. The medical system of claim 1,
wherein the filtration membrane is positioned within the interior volume to cause a reinfusion fluid received by the filtrate access to pass from the second side of the filtration membrane to the first side of the filtration membrane when the reinfusion fluid flows from the filtrate access to the filtration distal access, and
wherein the filtration membrane is positioned within the interior volume to cause a merged flow including the blood flow and the reinfusion fluid to flow from the first side to the dialyzer.

4. The medical system of claim 1, wherein the filtration body comprises a filtration inlet configured to receive a reinfusion fluid, wherein the filtration inlet is in fluid communication with the filtration distal access and the first side of the filtration membrane.

5. The medical system of claim 1, wherein the filtration body connector includes a bearing structure configured to transmit a force from the filtration body to the dialyzer or from the dialyzer to the filtration body when the filtration body connector mechanically mates with the dialyzer.

6. The medical system of claim 1, wherein the filtration body connector is configured to mechanically mate with the dialyzer when the filtration body is rotated relative to the dialyzer.

7. The medical system of claim 1, wherein the filtration body connector is configured to mechanically mate with the dialyzer when the filtration body is displaced in a direction toward the dialyzer or the dialyzer is displaced in a direction toward the filtration body.

8. The medical system of claim 1, wherein the filtration body defines a recess configured to receive a protrusion of the dialyzer when the filtration body connector mechanically mates with the dialyzer, and wherein the filtration body connector is defined within the recess.

9. The medical system of claim 1, wherein the filtration body defines the protrusion, and wherein the filtration body defines a filtration body recess surrounding the protrusion, the filtration body recess configured to receive the dialyzer when the filtration body connector removably mechanically mates with the dialyzer.

10. The medical system of claim 1, wherein the filtration body includes:
a proximal cap at the proximal end;
a distal cap at the distal end; and
a wall extending from the proximal cap to the distal cap, wherein the proximal cap defines the filtration proximal access, the distal cap defines the filtration distal access, and the wall defines the filtrate access.

11. The medical system of claim 1,
wherein the dialyzer comprises a hemodialysis membrane including a blood flow side and a dialysate side, wherein the dialyzer body defines a dialyzer interior volume, and wherein the hemodialysis membrane is positioned within the dialyzer interior volume, the dialyzer body comprising:
a dialyzer proximal access configured to receive a conditioned blood flow from the filtration body when the filtration body connector mechanically mates with the dialyzer body connector, wherein the dialyzer proximal access is in fluid communication with the blood flow side, and wherein the protrusion or the recess defined by the dialyzer body defines the dialyzer proximal access;
a dialyzer distal access in fluid communication with the blood flow side and the dialyzer proximal access;
a dialyzer inlet configured to receive dialysate from a dialysis machine, wherein the dialyzer inlet is in fluid communication with the dialysate side; and
a dialyzer outlet in fluid communication with the dialysate side and the dialyzer inlet.

12. The medical system of claim 11, wherein the hemodialysis membrane is configured to diffuse a uremic toxin from the blood side to the dialysate side when the conditioned blood flow contacts the blood flow side and the dialysate contacts the dialysate side.

13. The medical system of claim 9, wherein the filtration body connector is configured to threadably engage the dialyzer when the filtration body connector removably mechanically mates with the dialyzer.

14. The medical system of claim 9, wherein the filtration body includes a guiding surface defining the filtration body recess, and wherein the guiding surface faces a longitudinal axis defined by the filtration body and intersecting the proximal end and the distal end.

15. A medical system comprising:
a filtration membrane including a first side and a second side; and
a filtration body defining an interior volume between a proximal end and a distal end, wherein the filtration membrane is positioned within the interior volume, the filtration body comprising:
a proximal cap at the proximal end defining a filtration proximal access configured to receive a blood flow, wherein the filtration proximal access is in fluid communication with the first side of the filtration membrane;
a filtrate access in fluid communication with the second side of the filtration membrane;
a distal cap at the distal end defining a filtration distal access, wherein the filtration distal access is in fluid communication with the first side of the filtration membrane and the filtration proximal access, wherein the filtration distal access is configured to provide at least a portion of the blood flow to a dialyzer, wherein the filtration body defines a protrusion and the protrusion defines the filtration distal access, and wherein the filtration body defines a recess surrounding the protrusion; and
a filtration body connector secured to the distal cap, wherein the filtration body connector is defined on the protrusion,
wherein the filtration body connector is configured to removably mechanically mate with the dialyzer to enable the filtration distal access to provide the portion of the blood flow to the dialyzer, and
wherein the recess is configured to receive the dialyzer when the filtration body connector removably mechanically mates with the dialyzer.

16. The medical system of claim 15, further comprising the dialyzer, wherein the dialyzer comprises:
- a hemodialysis membrane including a blood flow side and a dialysate side, wherein the hemodialysis membrane is configured to diffuse a uremic toxin from the blood flow side to the dialysate side when a stream of blood contacts the blood flow side and a dialysate contacts the dialysate side; and
- a dialyzer body defining a dialyzer interior volume, wherein the hemodialysis membrane is positioned within the dialyzer interior volume, the dialyzer body comprising:
  - a dialyzer body connector secured to the dialyzer proximal end, wherein the dialyzer body connector is configured to removably mechanically mate with the filtration body connector to cause the filtration body connector to removably mechanically mate with the dialyzer;
  - a dialyzer proximal access configured to receive the stream of blood from the filtration body when the filtration body connector mechanically mates with the dialyzer body connector, wherein the dialyzer proximal access is in fluid communication with the blood flow side;
  - a dialyzer distal access in fluid communication with the blood flow side and the dialyzer proximal access;
  - a dialyzer inlet configured to receive the dialysate from a dialysis machine, wherein the dialyzer inlet is in fluid communication with the dialysate side; and
  - a dialyzer outlet in fluid communication with the dialysate side and the dialyzer inlet.

17. The medical system of claim 15, wherein the filtration body connector includes a bearing structure configured to transmit a force from the filtration body to the dialyzer or from the dialyzer to the filtration body when the filtration body connector mechanically mates with the dialyzer.

18. A method, comprising:
- removably mechanically mating a filtration body connector secured to a distal end of a filtration body with a dialyzer, wherein the mechanical mating is a removable mechanical mating, wherein the filtration body defines a filtration proximal access at a proximal end of the filtration body in fluid communication with a first side of a filtration membrane, a filtrate access in fluid communication with a second side of the filtration membrane, and a filtration distal access in fluid communication with the filtration proximal access and the first side of the filtration membrane, wherein the filtration body defines a protrusion configured to insert into a recess of the dialyzer when the filtration body connector mechanically mates with the dialyzer, wherein the protrusion defines the filtration distal access, and wherein the filtration body connector is defined on the protrusion, and wherein the filtration body defines a filtration body recess surrounding the protrusion, the filtration body recess configured to receive the dialyzer when the filtration body connector removably mechanically mates with the dialyzer; and establishing fluid communication between the filtration distal access and the dialyzer when the filtration body connector mechanically mates with the dialyzer.

19. The method of claim 18, wherein removably mechanically mating the filtration body connector with the dialyzer comprises inserting a protrusion defined by the dialyzer into a recess defined by the filtration body and surrounding the protrusion.

* * * * *